United States Patent [19]
Luther

[11] Patent Number: 5,120,317
[45] Date of Patent: Jun. 9, 1992

[54] VASCULAR/VENOUS ACCESS DEVICE AND METHOD OF UTILIZING AND FORMING THE SAME

[75] Inventor: Ronald B. Luther, Newport Beach, Calif.

[73] Assignee: Luther Medical Products, Inc., Tustin, Calif.

[21] Appl. No.: 703,241

[22] Filed: May 20, 1991

Related U.S. Application Data

[63] Continuation-in-part of Ser. No. 669,679, Mar. 14, 1991.

[51] Int. Cl.⁵ ............................................. A61M 5/00
[52] U.S. Cl. .................................... 604/158; 604/164
[58] Field of Search ............... 604/177, 164, 165, 158, 604/159, 161, 160, 168, 174, 198; 128/DIG. 26

[56] References Cited

U.S. PATENT DOCUMENTS

| | | | |
|---|---|---|---|
| 3,352,306 | 11/1967 | Hirsch | 604/164 |
| 4,249,541 | 2/1981 | Pratt | 604/165 |
| 4,627,841 | 12/1986 | Dorr | 604/158 |
| 4,772,264 | 9/1988 | Cragg | 604/165 |
| 4,828,549 | 5/1989 | Kunlo | 604/164 |
| 4,846,799 | 7/1989 | Tanaka et al. | 604/164 |
| 4,895,564 | 1/1990 | Farrell | 604/164 |
| 4,898,591 | 2/1990 | Jang et al. | 604/264 |
| 4,911,691 | 3/1990 | Aniuk et al. | 604/158 |
| 4,955,863 | 9/1990 | Walker et al. | 604/165 |
| 4,986,814 | 1/1991 | Burney et al. | 604/164 |

Primary Examiner—Paul J. Hirsch
Attorney, Agent, or Firm—Stetina and Brunda

[57] ABSTRACT

A vascular/venous access device is comprised of a catheter having a stop formed at the distal end thereof, and a needle cannula having a corresponding stop formed at the distal end therof, the needle cannula being disposed within the catheter such that the catheter stop and needle cannula stop abut to prevent the catheter from traveling axially upward relative to the needle cannula during the insertion process. The catheter stop may comprise a material which softens when exposed to blood such that the stop is generally rigid during insertion of the catheter into a vein and becomes more flexible after the catheter resides in the vein. The catheter stop may comprise a region of reduced diameter and the cannula stop may comprise a region of increased diameter. The needle cannula may be disposed within the catheter with the sharp end of the needle cannula extending outwardly beyond the distal end of the catheter and the opposite end of the needle extending through the wall of the catheter between the distal end and proximal end of the catheter. A telescoping cannula assembly may be utilized wherein the distal end of an outer cannula defines the cannula stop and wherein the inner cannula may be withdrawn into the outer cannula prior to withdrawing the telescoping cannula assembly from the catheter to prevent damage to the inside of the catheter which might otherwise be inflicted by the sharp point of the inner needle cannula.

17 Claims, 2 Drawing Sheets

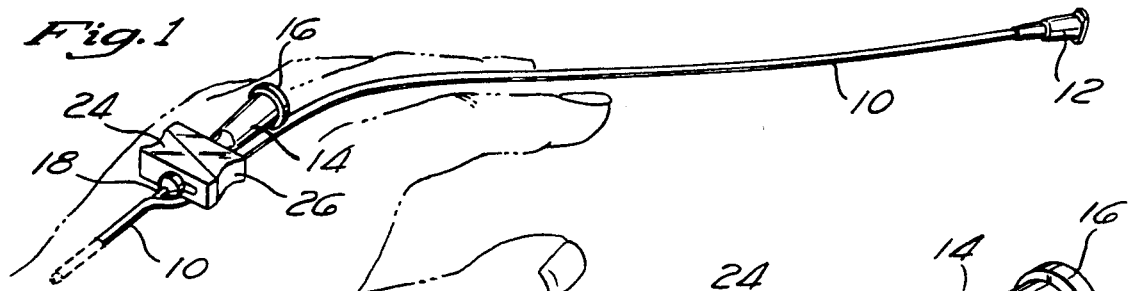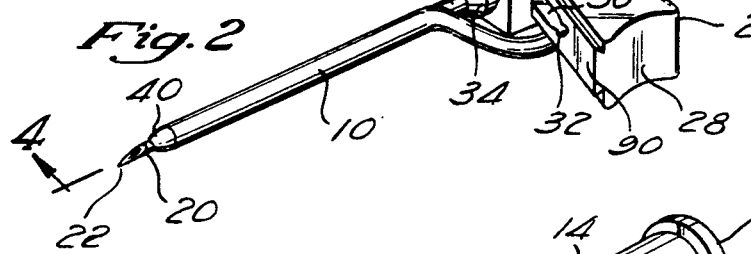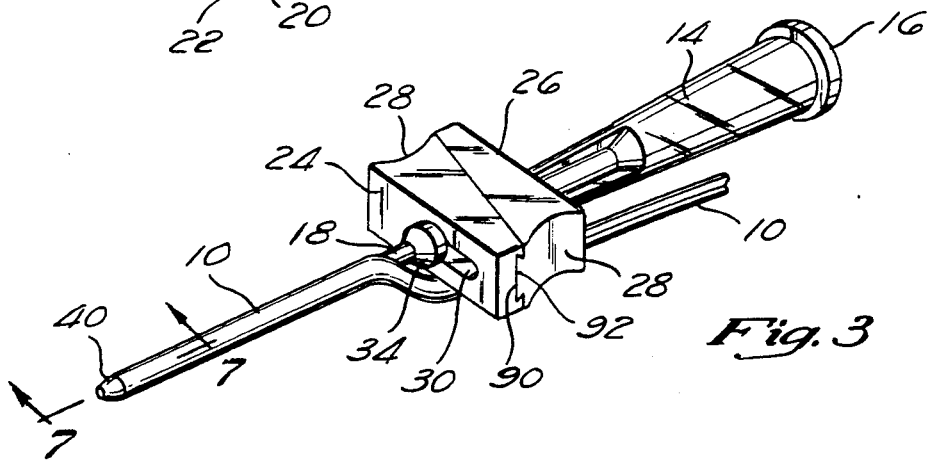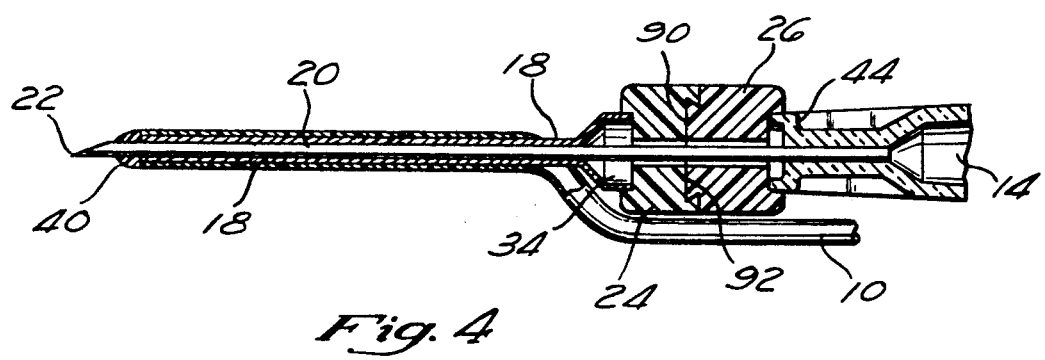

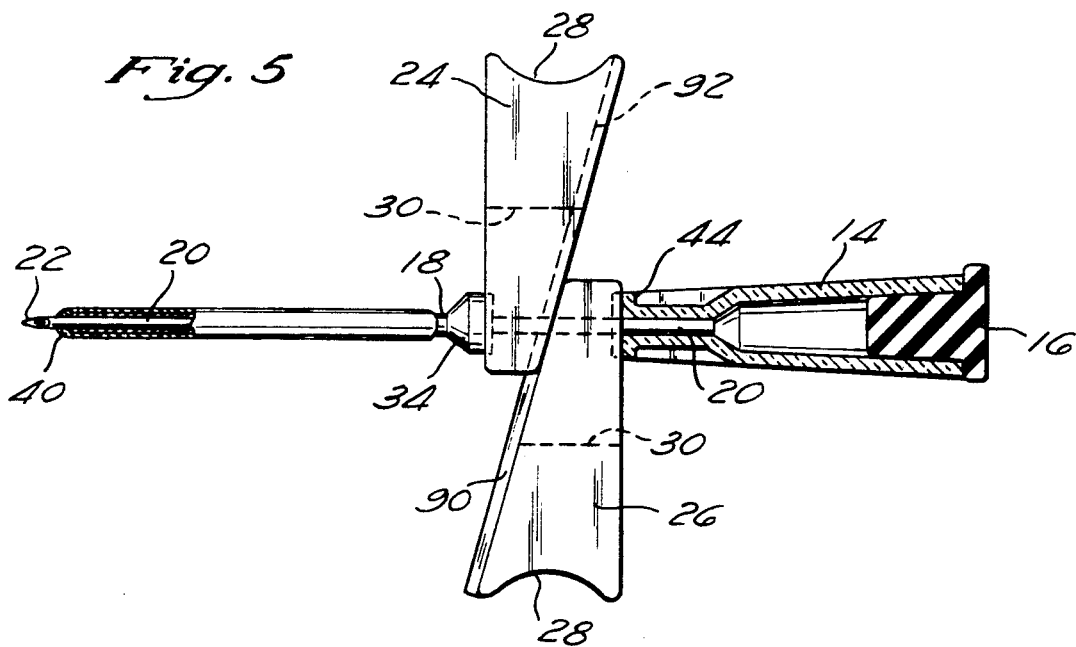
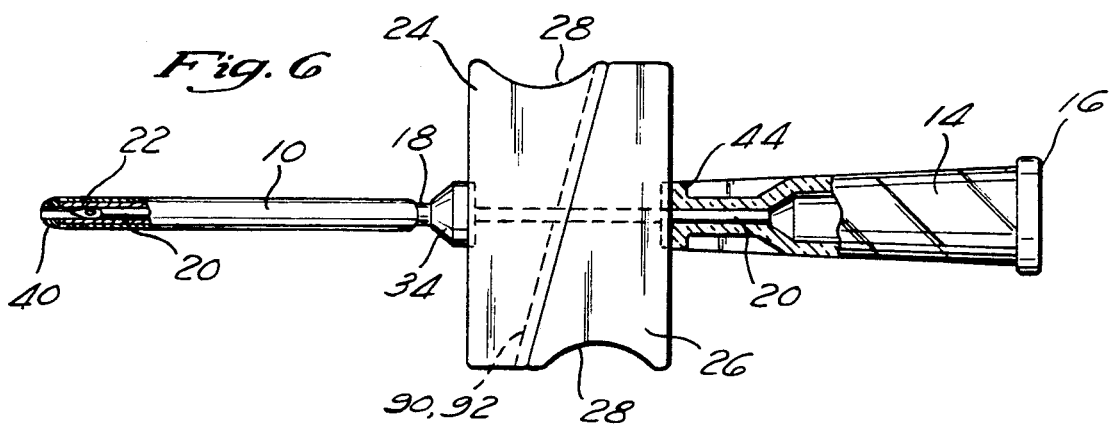
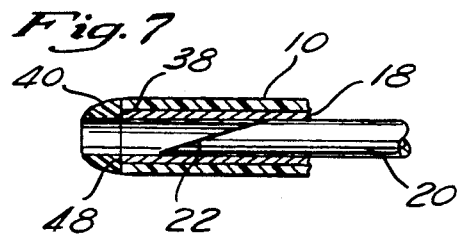
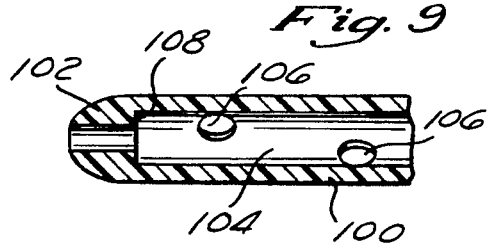
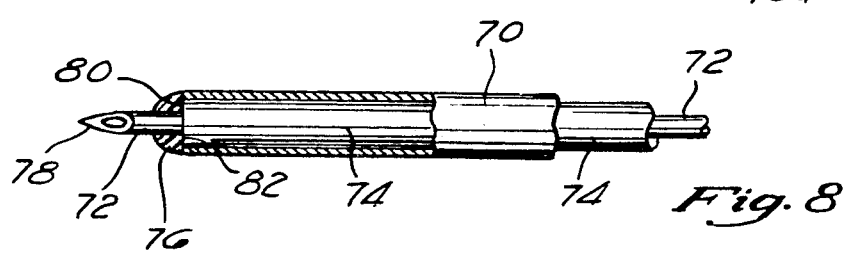

VASCULAR/VENOUS ACCESS DEVICE AND METHOD OF UTILIZING AND FORMING THE SAME

RELATED APPLICATIONS

This is a continuation-in-part application of U.S. Ser. No. 07/669,679, filed on Mar. 14, 1991, and entitled "VASCULAR/VENOUS ACCESS DEVICE AND METHOD OF UTILIZING AND FORMING THE SAME".

FIELD OF THE INVENTION

The present invention relates generally to medical insertion devices and more particularly to a venous or vascular access device for introducing any desired length of catheter into the vascular system.

BACKGROUND OF THE INVENTION

Vascular/venous access devices for introducing catheters into a patient's vascular system are well known. The simplest of such devices comprises a through-the-needle catheter having a cannula which generally comprises a metal needle inserted into the patient's vein and through which a catheter may subsequently be introduced. A common problem associated with the use of such prior art through-the-needle catheter systems arises in removing the cannula after the catheter has been introduced into the vein. Since the cannula is typically comprised of a rigid metal needle, it is desirable to remove the cannula from the patient's vein after insertion of the catheter to prevent trauma to the vein caused by the cannula's rigid structure and/or sharp tip. However, once the catheter has been inserted into the vein, the cannula can typically only be removed by retracting the same upwardly along the catheter, thereby exposing the patient as well as administering personnel to accidental contact with the cannula.

In recognizing the discomfort and extraction problems of the cannula associated with through the needle catheter systems, over-the-needle catheter systems have been widely utilized for venous access applications. In such over-the-needle catheter systems, a thin catheter having a hub at its proximal end is placed over a rigid cannula, such as a needle, whereby the cannula as well as the catheter may be simultaneously inserted into the vein of a patient. Once the cannula and catheter and have been introduced into the vein, the cannula may be withdrawn from the interior of the catheter leaving the catheter disposed within the patient's vein. Subsequently, required administration line communication can be effectuated with the catheter by interconnection with its hub mounted to the proximal end of the catheter. However, due to such over-the-needle catheters being inserted into the vein of the patient concurrently with the rigid cannula, such over-the-needle catheters must possess sufficient rigidity to prevent the same from traveling axially upward relative to the cannula during the insertion process. As such, over-the-needle catheters are limited in their axial length and are incapable of being inserted upwardly through the length of the vein or artery without causing trauma and/or puncture to the vein.

In recent years, the desirability of utilizing a peripherally inserted central catheter (PICC) line into a patient for medical applications has become widespread. In such PICC line applications, a flexible catheter must be introduced into the vascular system of a patient and subsequently be manipulated to allow the catheter to wind its way upwardly through the vascular system to a desired location. Due to the requirement of advancing the catheter upwardly through the vascular system, the catheter must be formed from a soft, biocompatible, pliable, and flexible material which is capable of winding through and extending through substantial axial lengths of the vascular system, i.e. from two to thirty inches or more, without causing trauma to the vascular system or puncturing therethrough. In view of such requirements, heretofore, through-the-needle catheter systems have been typically utilized wherein after venous insertion, the cannula is retained within the patient and the desired length of catheter is inserted through the cannula and into the vein of the patient. In such applications blood leakage is commonplace, thus exposing administering personnel to substantial health risks, such as those associated with the AIDS virus, hepatitis, and other infectious diseases.

In view of these concerns, recently an over-the-needle catheter system has been introduced specifically adapted for PICC line applications which attempts to minimize accidental exposure of medical personnel to patient's blood. This particular venous access device is manufactured by Menlo Care, Inc. of Palo Alto, Calif. and is marketed under the trademark LANDMARK venous access device.

The LANDMARK venous access device facilitates the insertion of a limited length (i.e. finite length) of catheter into a patient's vein while permitting the needle to be withdrawn after the initial insertion via a stylet extending through the catheter and then stowed within a protective sheath to prevent accidental puncture and/or exposure. However, the LANDMARK venous access device is strictly limited in the length of the catheter provided, thus necessitating the correct initial selection of catheter length. Additionally, the LANDMARK venous access device is relatively complex in its construction, thus increasing the cost of fabrication and consequently increasing its associated patient cost. Furthermore, the LANDMARK venous access device is relatively complicated to use, requiring a significant amount of training and manipulative skill.

In view of the shortcomings of the prior art, it is desirable to provide an improved vascular/venous access device which would permit the introduction of an unlimited length of catheter into a patient's vascular system which facilitates removal of the needle to prevent accidental punctures and/or exposure; which is simple and inexpensive to fabricate; and which requires a minimum of training and manipulative skill to practice.

SUMMARY OF THE INVENTION

The present invention specifically addresses and alleviates the above-mentioned deficiencies associated in the prior art. More particularly, the present invention comprises a vascular/venous access device which is comprised of a catheter having a stop formed at the distal end thereof, and a needle cannula having a corresponding stop formed at the distal end thereof, the needle cannula being disposed within the catheter such that the catheter stop and needle cannula stop abut to prevent the catheter from traveling axially upward relative to the needle cannula as the needle cannula is inserted into a patient's vein.

The catheter stop may comprise a material which softens when exposed to blood such that the cannula stop is generally rigid during insertion of the catheter into a vein and becomes more flexible after the catheter resides in the vein. The catheter stop may comprise a region of reduced diameter and the needle cannula stop may comprise a region of increased diameter. The catheter stop may thus be defined by a reduced annular shoulder which engages or abuts a corresponding annular shoulder formed upon the outer portion of the end of the needle cannula. The needle cannula may be disposed within the catheter with the sharp end of the needle cannula extending outwardly beyond the distal end of the catheter and the opposite end of the needle extending through the wall of the catheter at a point between the distal end and proximal end of the catheter. A telescoping cannula assembly may be utilized wherein the distal end of an outer cannula defines the cannula stop and wherein an inner needle cannula may be withdrawn into the outer cannula prior to withdrawing the telescoping cannula assembly from the catheter to prevent damage to the inside of the catheter which might otherwise be inflicted by the sharp point of the inner needle cannula.

BRIEF DESCRIPTION OF THE DRAWINGS

FIG. 1 is a perspective view of the vascular/venous access device of a first embodiment of the present invention after insertion into a vein on the back of a patient's hand;

FIG. 2 is a perspective view of the vascular/venous access device of FIG. 1 prior to insertion;

FIG. 3 is a perspective view of the vascular/venous access device of FIG. 1 having the sharp point of the inner cannula withdrawn into the outer cannula and catheter as would occur immediately prior to withdrawal of the two cannulas during the insertion process;

FIG. 4 is a cross-sectional side view of the vascular/venous access device of FIG. 1 showing the sharp point of the inner cannula extending from the catheter;

FIG. 5 is a top view, partly in section, of the vascular/venous access device of FIG. 1 showing the sharp tip of the inner cannula extending from the catheter and the actuation means in their outboard positions;

FIG. 6 is a side view, partly in section, of the vascular/venous access device of FIG. 1 showing the two actuation means in their inboard positions and showing the sharp point of the inner cannula withdrawn into the catheter and outer cannula;

FIG. 7 is an enlarged cross-sectional side view of the distal portion of the vascular/venous access device of FIG. 1 showing the sharp point of the inner cannula disposed within the outer cannula and catheter;

FIG. 8 is an enlarged cross-sectional top view of the distal portion of the vascular/venous access device of a second embodiment of the present invention showing a needle cannula detent formed as an integral part of the needle cannula; and FIG. 9 is an enlarged cross-sectional side view of a unitary construction vascular/venous access device wherein the catheter stop is formed of the same material as the remainder of the catheter and as an integral part thereof.

DETAILED DESCRIPTION OF THE PREFERRED EMBODIMENTS

The detailed description set forth below in connection with the appended drawings is intended as a description of the presently preferred embodiments of the invention, and is not intended to represent the only forms in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The vascular/venous access device of the present invention is illustrated in FIGS. 1-9 which depict two presently preferred embodiments of the invention. FIGS. 1-7 depict a first embodiment having a telescoping cannula and FIGS. 8-9 depict a second embodiment having a stop formed as an integral portion of the needle cannula.

Referring now to FIGS. 1-7, the vascular/venous access device of the present invention generally comprises a catheter 10, an outer cannula 18 inserted into the catheter 10 through the side wall thereof, and an inner or needle cannula 20 slidably disposed within the outer cannula 18, the needle cannula 20 having a sharp point 22 and being in fluid communication with a flash chamber 14.

Two actuation means 24 and 26, preferably wedges or the like, slidably disposed relative to each other, have slots 30 formed therein. The needle cannula 20 is received by the two slots 30. A hub 34 formed upon the proximal end of the outer cannula 18 engages the slot 30 in the first actuation means 24 and a hub 44 formed upon the distal end of the flash chamber 14 engages the slot 30 in the second actuation means 26. A region of reduced width 32 is formed at the outboard portion of each slot 30. The region of reduced width 32 is configured to function as a detent and snap over the needle cannula 20, thereby locking each actuation means 24 and 28 in position relative to the needle cannula 20 when snapped thereover. A concave surface 28 is preferably formed upon the outboard portion of each actuation means 24 and 26 to facilitate manipulation thereof.

The two actuation means 24 and 26 are slidably engaged to prevent relative rotation thereof. They are preferably dovetailed together by receiving a male dovetail member 90 formed upon one actuation means 26 slidably into a female dovetail member 92 formed within the other actuation means 24. Thus, the two actuation means 24 and 26 are free to reciprocate or slide back and forth relative to one another.

A porous hydrophobic plug 16 is inserted into the flash chamber 14 to facilitate the escape of air as blood enters the flash chamber 14. A Luer lock 12 is preferably formed upon the proximal end of the catheter 10. The flash chamber 14 is preferably configured to receive a Luer lock syringe after removing the porous plug.

A comparatively rigid softenable material 40 is formed upon the distal end of the catheter 10. The softenable material 40 has an inner diameter (best seen in FIG. 7) which is less than the outer diameter of the outer cannula 18 such that the proximal surface 38 of the softenable material 40 forms a reduced diameter annular shoulder or catheter stop The distal end 48 of the outer cannula 18 abuts or engages the softenable material 40 and thus forms a cannula stop. The softenable material 40 defines the distal tip of the catheter 10. The proximal surface 38 of the softenable material 40 thus prevents the distal end 48 of the cannula 18 from extending therethrough.

Various hydrophilic polymer materials which are comparatively rigid when dry, yet soften and expand upon contact with blood or other fluids, may be utilized as the softenable material 40 of the present invention. Since the venous/vascular access device of the present invention may be used in various applications, such as to extract fluid from the thorax or to drain the bladder, the softenable material 40 will preferably soften and expand upon contact with any water-containing fluid. In the preferred embodiment, this particular hydrophilic polymer material comprises a hydrophilic polyurethane, such as that disclosed in further detail in Applicant's copending U.S. patent application Ser. No. 07/669,679, filed on Mar. 14, 1991, and in U.S. Pat. No. 4,439,583, entitled POLYURETHANE DIACRYLATE COMPOSITIONS USEFUL IN FORMING CANNULE, the contents of both of which are expressly incorporated by reference herein. However, those skilled in the art will recognize that numerous substitute materials possessing such a selective softening property are contemplated herein. More particularly, a suitable material comprises a thermally softening polymer compound which, upon experiencing a thermal gradient such as that encountered between ambient and patient residence temperatures, the polymer rapidly softens and becomes more flexible. An example of such a thermally softening compound is manufactured by Thoratec Laboratories Corporation in Berkeley, Calif. Additionally, in the preferred embodiment the remainder of the catheter 10 is formed of a soft, flexible polyurethane polymer suitable for non-traumatic travel through the vascular system of a patient, such as Vialon, a catheter material marketed by Becton Dickinson of Sandy, Utah, under the trademark INSYTE. However, those skilled in the art will recognize that alternative polymers are additionally contemplated herein. Softening of the softenable material 40 permits the catheter to be fed through the vascular system with a reduced probability of causing trauma to the vascular walls with the tip of the catheter. Expansion of the softenable material 40 prevents the region of reduced diameter formed by the softenable material 40 from restricting fluid flow, since such expansion results in an increased inner diameter of the softenable material.

The softenable material 40 may be butt welded to the catheter 10. A thin coating of a polymer, preferably hydrophilic/polyurethane material, may then be formed over the softenable material 40 and the distal end of the catheter 10 to further secure the softenable material 40 to the catheter 10. The thin coating may comprise the same material as the softenable material 40.

Having thus described the structure of the vascular/venous access device of the present invention, it may be helpful to describe the use thereof. The vascular/venous access device is initially configured as illustrated in FIG. 2. The actuation means 24 and 26 are disposed at their outboard positions and the point 22 of the needle cannula 20 extends from the catheter 10.

The vascular/venous access device is inserted into a vein or other vessel in the conventional manner. The actuation means 24 and 26 may serve as a convenient handle during manipulation of the device. The outer cannula 18 prevents the distal end of the catheter 10 from moving axially up the outer cannula as the device is inserted. The stop formed, by the distal surface 48 of the outer cannula 18 abuts the stop formed by the proximal surface 38 of the softenable material 40 to prevent such motion. Thus, the catheter 10 is urged into the vein along with the inner needle cannula 20 and the outer cannula 18.

As in conventional insertion devices, when the point 22 of the needle catheter 20 enters a vein, blood may be observed entering the flash chamber 14. The porous hydrophobic plug 16 may be removed such that a Luer lock syringe or the like may be connected thereto for the immediate administration of medication, to collect blood samples, or to further verify correct placement.

Once the catheter 10 has been inserted, the inner or needle 20 and outer 18 catheters may be removed therefrom. Removal is effected by first compressing the two actuation means 24 and 26 together or inboard, such that the outer cannula hub 34 and the flash chamber hub 44 are forced apart to withdraw the point 22 into the outer cannula 18, as depicted in FIG. 7. Withdrawal of the point 22 into the outer cannula 18 thus sheaths the point 22 of the needle cannula 20 and thereby prevents the point 22 from damaging the inner diameter of the catheter 10 as the two cannulae are withdrawn therefrom. After the two actuation means 24 and 26 have been fully compressed inboard, as shown in FIG. 6, the needle cannula 20 and outer cannula 18 are withdrawn from the catheter 10 by grasping the catheter 10 and slowly pulling the actuation means 24 and 26 away from the catheter 10. A desired length of catheter 10 may subsequently be urged into the vein.

Referring now to FIG. 8, a second embodiment of the vascular/venous access device of the present invention is depicted. In the second presently preferred embodiment a stop is formed directly upon the needle cannula to prevent the catheter from traveling axially therealong during insertion thereof. The stop is formed by providing a region of increased diameter 74 along the length of the needle catheter 72. The point where the needle cannula 72 increases in diameter thus forms a stop 80 which abuts the proximal surface 82 of the softenable material 76. The needle cannula 72 and the region of increased diameter 74 are formed as an integral unit such that they will be withdrawn together. The second embodiment is thus configured such that its needle cannula 72 would resemble the needle cannula 20 of the first embodiment if the needle cannula 20 and the outer cannula 18 of the first embodiment were to be formed as an integral unit. Those skilled in the art will recognize that various means for forming a stop upon the needle cannula are likewise suitable. Thus, bumps, ridges, protrusions, or the like may be suitable for use as a cannula stop in the practice of the vascular/venous access device of the present invention. The use of a region of increased diameter is preferred because it provides an even and continuous surface which supports the catheter 70. Unlike the vascular/venous access device of the first embodiment, the point 78 of the vascular/venous access device of the second embodiment is not sheathed or protected as the needle cannula 72 is withdrawn from the catheter 70 after insertion. Thus, care must be exercised not to scratch or otherwise damage the interior surface of the catheter 70 during withdrawal.

The vascular/venous access device of the second embodiment, like that of the first embodiment, is inserted into the catheter at a point between the distal and proximal ends of the catheter 70 such that the point 78 of the needle cannula 72 extends beyond the distal end of the catheter and the proximal end of the needle cannula 74 extends through the wall of the catheter. The vascular/venous access device of the second embodiment is inserted into a vein by firmly grasping the catheter 70 such that the catheter 70 is locked into position relative to the needle cannula 72. The vascular/venous access device of the second embodiment is then inserted into a vein in the conventional manner. Optionally, a clamping device (not shown) may be utilized to look the catheter 70 into position relative to the region of increased diameter 74 of the needle cannula 72.

Referring now to FIG. 9, a unitary construction vascular/venous access device 100 has a catheter stop 108 formed of the same material as the rest of the catheter, preferably of VIALON.

The catheter stop 108 is preferably provided by forming a reduced diameter annular shoulder or region of reduced diameter 102 at the distal end of the unitary construction catheter 100. Being comprised of the same material as the remainder of the catheter 104, the region o reduced diameter does not substantially soften and/or expand as to those of FIGS. 1–8. A needle cannula 74 having a corresponding shoulder of increased diameter or needle cannula stop 80, such as that shown in FIG. 8, may be inserted through the unitary construction catheter 100 until the cannula stop 80 abuts the catheter stop 108. The cannula stop 80 cooperates with the catheter stop 108 to prevent the distal end of the catheter 100 from traveling axially upward as the catheter 100 is inserted.

At least one aperture 106 is formed in the unitary construction catheter4 100 proximate the region of reduced diameter 102 such that fluid flow through the unitary construction catheter 100 is not substantially reduced by the region of reduced diameter 102. Thus, the flow rate for the unitary construction catheter 100 is similar to that of a contemporary catheter of the same inner diameter.

It is understood that the exemplary vascular/venous access device described herein and shown in the drawings represents only a presently preferred embodiment of the invention. Indeed, various modifications and additions may be made to such embodiment without departing from the spirit and scope of the invention. For example, the actuation means need not be sized and configured as described and illustrated, but rather may be of any configuration wherein they may be easily grasped, and are movable relative to one another such that they may be utilized to cause the inner cannula to withdraw into the outer cannula. Also, those skilled in the art will recognize that various configurations of catheter stops and cannula stops are likewise suitable. Thus, these and other modifications and additions may be obvious to those skilled in the art and may be implemented to adapt the present invention for use in a variety of different applications.

What is claimed is:

1. A vascular/venous access device comprising:
   (a) a catheter having a stop formed at the distal end thereof; and
   (b) a needle cannula having a corresponding stop formed at the distal end thereof and a lumen formed therein, said needle cannula being disposed within said catheter, said cannula stop abutting said catheter stop to prevent the distal end of said catheter from traveling axially as said needle cannula is inserted, said needle cannula disposed within said catheter with the sharp end of the needle cannula extending outwardly beyond the distal end of the catheter and the opposite end of the needle cannula extending through the wall of the catheter between the distal end and proximal end of the catheter; and
   (c) a flash chamber formed upon the proximal end of said needle cannula.

2. The vascular/venous access device as recited in claim 1 wherein said catheter stop defines the distal tip of said catheter and comprises a material which softens when exposed to blood such that the catheter stop is generally rigid during insertion of the catheter into a vein and becomes more flexible after the catheter resides within the vein.

3. The vascular/venous access device as recited in claim 1 wherein said catheter stop comprises a region of reduced diameter and the cannula stop comprises a region of increased diameter.

4. The vascular/venous access device as recited in claim 3 further comprising at least one aperture formed in said catheter proximate said region of reduced diameter such that fluid flow through said catheter is not substantially reduced by said region of reduced diameter.

5. A telescoping cannula assembly vascular/venous access device comprising:
   (a) a catheter having a stop formed at the distal end thereof;
   (b) a first cannula disposed within said catheter, said first cannula abutting said catheter stop such that said first cannula is prevented from extending from said catheter;
   (c) a second cannula disposed with said first cannula, the distal end of said second cannula having a point formed thereon and a lumen formed therein;
   (d) said second cannula disposed within said catheter with the sharp end of the needle cannula extending outwardly beyond the distal end of the catheter and the opposite end of the second cannula extending through the wall of the catheter between the distal end and the proximal end of the catheter; and
   (e) a flash chamber formed upon the proximal end of said second cannula.

6. The telescoping cannula assembly and the vascular/venous access device as recited in claim 5 wherein said catheter stop defines the distal tip of said catheter and comprises a material which softens when exposed to blood such that the catheter stop is generally rigid during insertion of the catheter into a vein and becomes more flexible after the catheter resides within the vein.

7. The telescoping cannula assembly vascular/venous access device as recited in claim 6 wherein said catheter stop comprises a region of reduced diameter and said first cannula has an outside diameter greater than the inside diameter of said catheter stop.

8. The telescoping cannula assembly vascular/venous access device as recited in claim 7 wherein said second cannula is slidably disposed within said first cannula.

9. The telescoping cannula assembly vascular/venous access device as recited in claim 10 further comprising:
   (a) a hub formed upon the proximal end of the first cannula;

(b) a hub formed upon the distal end of said flash chamber;
(c) a first actuation means having a first slot formed therein, said first slot receiving said second cannula;
(d) a second actuation means having a second slot formed therein, said second slot receiving said second cannula; and
(e) wherein the urging of said first and second actuation means toward each other causes the point of said second cannula to withdraw into said first cannula.

10. The telescoping cannula assembly vascular/venous access device as recited in claim 9 wherein said flash chamber is configured in a Luer lock fashion.

11. A telescoping cannula assembly vascular/venous access device comprising:
(a) a catheter having a stop formed at the distal end thereof, said stop defining the distal tip of said catheter and comprising a material which softens when exposed to blood such that the catheter stop is generally rigid during insertion of the catheter into a vein and becomes more flexible after the catheter resides within the vein, said stop comprising a region of reduced diameter;
(b) a first cannula disposed within said catheter, said first cannula abutting said catheter stop such that said first cannula is prevented from extending from said catheter, said first cannula having an outside diameter greater than the inside diameter of said catheter stop;
(c) a second cannula slidably disposed with said first cannula, the distal end of said second cannula having a point formed thereon, said second cannula disposed within said catheter with the sharp end of the second cannula extending outwardly beyond the distal end of the catheter and the opposite end of the needle cannula extending through the wall of the catheter between the distal end and the proximal end of the catheter;
(d) a hub formed upon the proximal end of the first cannula;
(e) a flash chamber formed upon the proximal end of said second cannula;
(f) a hub formed upon the distal end of said flash chamber;
(g) a first actuation means having a first slot formed therein, said first slot receiving said second cannula;
(h) a second actuation means having a second slot formed therein, said second slot receiving said second cannula; and
(i) wherein the urging of said first and second actuation means toward each other causes the point of said second cannula to withdraw into said first cannula.

12. The telescoping cannula assembly vascular/venous access device as recited in claim 11 wherein said flash chamber is configured in a Luer lock fashion.

13. A vascular/venous access device comprising:
(a) a catheter having a distal end;
(b) a first cannula disposed within at least a portion of said catheter and extending approximately to the distal end thereof;
(c) a second cannula slidably disposed within said first cannula and having a point formed therein, the point extending from said first cannula and said catheter;
(d) actuator means for withdrawing the point of said second cannula into said first cannula;
(e) wherein the withdrawal of the point of said second cannula into said first cannula facilitates the removal of said second cannula from said catheter while mitigating the potential for damaging said catheter with the point of said second cannula.

14. The vascular/venous access device as recited in claim 13 wherein said actuator means for withdrawing comprises:
(a) a first hub formed upon the proximal end of said first cannula;
(b) a second hub formed upon the proximal end of said second cannula; and
(c) means for urging said first and second hubs away from one another.

15. The vascular/venous access device as recited in claim 14 wherein said urging means comprises at least one wedge which forces said first and second hubs away from one another as said wedge is urged therebetween.

16. The vascular/venous access device as recited in claim 14 wherein said urging means comprises first and second slidably interlocking wedges which force said first and second hubs away from one another as said first and second wedges are urged toward each other.

17. The vascular/venous access device as recited in claim 16 further comprising:
(a) a lumen formed within said second cannula; and
(b) a flash chamber in fluid communication with said lumen.

* * * * *